(12) United States Patent
Sambelashvili et al.

(10) Patent No.: US 11,724,028 B2
(45) Date of Patent: Aug. 15, 2023

(54) DETECTION OF PUMP THROMBOSIS

(71) Applicant: Medtronic, Inc., Minneapolis, MN (US)

(72) Inventors: Aleksandre T. Sambelashvili, Maple Grove, MN (US); David A. Anderson, Stanchfield, MN (US); James K. Carney, Roseville, MN (US); David M. Steinhaus, Minneapolis, MN (US); Narendra K. Simha, Falcon Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 475 days.

(21) Appl. No.: 17/007,342

(22) Filed: Aug. 31, 2020

(65) Prior Publication Data
US 2020/0397962 A1 Dec. 24, 2020

Related U.S. Application Data

(63) Continuation of application No. 15/969,030, filed on May 2, 2018, now Pat. No. 10,765,790.
(Continued)

(51) Int. Cl.
*A61M 5/172* (2006.01)
*A61M 60/113* (2021.01)
(Continued)

(52) U.S. Cl.
CPC .......... *A61M 5/172* (2013.01); *A61M 60/113* (2021.01); *A61M 60/148* (2021.01);
(Continued)

(58) Field of Classification Search
CPC .. A61M 5/172; A61M 60/113; A61M 60/148; A61M 60/422; A61M 60/515;
(Continued)

(56) References Cited

U.S. PATENT DOCUMENTS 6,688,861 B2 2/2004 Wampler
7,265,676 B2 9/2007 Gordon et al.
(Continued)

FOREIGN PATENT DOCUMENTS

| CN | 105429036 A | 3/2016 |
|----|-------------|--------|
| JP | 2009240348 A | 10/2009 |

(Continued)

OTHER PUBLICATIONS

Hubbert, et al., "Acoustic Analysis of a Mechanical Circulatory Support," Artif Organs, vol. 38 No 7, Jul. 2014, pp. 593-598.
(Continued)

*Primary Examiner* — Christopher A Flory
(74) *Attorney, Agent, or Firm* — Shumaker & Sieffert, P.A.

(57) ABSTRACT

The disclosure describes systems and techniques for detection of pump thrombosis in mechanical circulatory support (MCS) devices. An example pump thrombosis detection system includes a transducer and processing circuitry. The transducer may be configured to generate a signal representative of a mechanical wave from a mechanical circulatory support device. The processing circuitry is communicatively coupled to the transducer. The processing circuitry may be configured to determine an indication of pump thrombosis based on the signal and, based on the indication of pump thrombosis, control the pump thrombosis detection system to at least one of generate an alert or initiate an intervention.

22 Claims, 5 Drawing Sheets

Related U.S. Application Data

(60) Provisional application No. 62/632,904, filed on Feb. 20, 2018.

(51) Int. Cl.

| | | |
|---|---|---|
| *A61M 60/148* | (2021.01) | |
| *A61M 60/422* | (2021.01) | |
| *A61M 60/857* | (2021.01) | |
| *A61M 60/538* | (2021.01) | |
| *A61M 60/515* | (2021.01) | |
| *A61M 60/585* | (2021.01) | |
| *A61M 60/178* | (2021.01) | |
| *A61M 60/279* | (2021.01) | |
| *A61M 60/237* | (2021.01) | |
| *A61M 60/232* | (2021.01) | |
| *A61M 60/30* | (2021.01) | |

(52) U.S. Cl.
CPC ........ *A61M 60/178* (2021.01); *A61M 60/232* (2021.01); *A61M 60/237* (2021.01); *A61M 60/279* (2021.01); *A61M 60/30* (2021.01); *A61M 60/422* (2021.01); *A61M 60/515* (2021.01); *A61M 60/538* (2021.01); *A61M 60/585* (2021.01); *A61M 60/857* (2021.01); *A61M 2205/18* (2013.01); *A61M 2205/3303* (2013.01); *A61M 2205/3317* (2013.01); *A61M 2205/3375* (2013.01); *A61M 2205/3507* (2013.01); *A61M 2205/3553* (2013.01); *A61M 2205/3584* (2013.01); *A61M 2205/50* (2013.01); *A61M 2205/502* (2013.01)

(58) Field of Classification Search
CPC .............. A61M 60/538; A61M 60/857; A61M 2205/18; A61M 2205/3303; A61M 2205/3317; A61M 2205/3375; A61M 2205/3553; A61M 2205/3584; A61M 2205/50; A61M 2205/502
See application file for complete search history.

(56) References Cited

U.S. PATENT DOCUMENTS

| | | | |
|---|---|---|---|
| 7,699,586 B2 | 4/2010 | Larose et al. | |
| 8,403,823 B2 | 3/2013 | Yu et al. | |
| 8,870,739 B2 | 10/2014 | Larose et al. | |
| 10,765,790 B2* | 9/2020 | Sambelashvili | ..... A61M 60/113 |
| 2002/0115940 A1* | 8/2002 | Ferek-Petric | ...... A61N 1/36585 600/513 |
| 2003/0045772 A1 | 3/2003 | Reich | |
| 2006/0136012 A1 | 6/2006 | Koshiol | |
| 2008/0319544 A1 | 12/2008 | Yaegashi | |
| 2009/0157057 A1 | 6/2009 | Ferren | |
| 2010/0234786 A1 | 9/2010 | Fulkerson et al. | |
| 2011/0112354 A1 | 5/2011 | Nishimura et al. | |
| 2011/0313238 A1 | 12/2011 | Reichenbach | |
| 2012/0235634 A1 | 9/2012 | Hall | |
| 2013/0190621 A1 | 7/2013 | Somberg | |
| 2015/0018600 A1 | 1/2015 | Zilbershlag | |
| 2015/0080748 A1 | 3/2015 | Hubbert | |
| 2015/0133721 A1 | 5/2015 | Roth | |
| 2015/0174307 A1* | 6/2015 | Eckman | .............. A61M 60/196 600/17 |
| 2016/0310077 A1* | 10/2016 | Hunter | ................. A61B 5/6862 |
| 2017/0049945 A1 | 2/2017 | Halvorsen et al. | |
| 2017/0119256 A1 | 5/2017 | Demou et al. | |
| 2017/0209632 A1 | 7/2017 | Pierce | |
| 2018/0126053 A1 | 5/2018 | Zilbershlag | |
| 2019/0125932 A1 | 5/2019 | Leonhardt | |
| 2019/0255235 A1 | 8/2019 | Sambelashvili et al. | |

FOREIGN PATENT DOCUMENTS

| | | |
|---|---|---|
| WO | 199814225 A2 | 4/1998 |
| WO | 2009127683 A1 | 10/2009 |

OTHER PUBLICATIONS

Kaufmann, et al., "Acoustic Spectral Analysis for Determing Pump Thrombosis in Rotary Blood Pumps," ASAIO Journal 2014, Sept./Oct. 2014, vol. 60, No. 5, pp. 502-507.

Prosecution History from U.S. Appl. No. 15/969,030, dated Feb. 19, 2020 through Jun. 11, 2020, 44 pp.

Rogers, M.D., "Intrapericardial Left Ventricular Assist Device for Advanced Heart Failure," The New England Journal of Medicine, Feb. 2, 2017, pp. 451-460.

Uriel, MD., "Device thrombosis in HeartMate II continuous-flow left ventricular assist devices: A multifactorial phenomenon," The Journal of Heart and Lung Transplantation, vol. 33, No. 1, Jan. 2014, pp. 51-59.

Yost, et al., "Acoustic Characterization of Axial Flow Left Ventricular Assist Device Operation in Vitro and In Vivo," ASAIO Journal 2016, Jan./Feb. 2016, vol. 62, No. 1, pp. 46-55.

First Office Action and Search Report, and translation thereof, from counterpart Chinese Application No. 201980014253.5 dated Feb. 11, 2023, 20 pp.

\* cited by examiner

DETECTION OF PUMP THROMBOSIS

This application is a continuation of U.S. patent application Ser. No. 15/969,030, filed May 2, 2018, which claims the benefit of U.S. Provisional Patent Application No. 62/632,904, filed Feb. 20, 2018, the entire content of each of these applications is incorporated herein by reference.

TECHNICAL FIELD

This disclosure relates to systems and methods for detecting pump thrombosis, such as of a mechanical circulatory support device.

BACKGROUND

Heart disease is one of the leading causes of death and hospitalization among the elderly. The number of patients that reach an advanced phase of heart disease (e.g., end stage heart failure, refractory heart failure, or terminal heart failure) continues to increase due to improvements in the treatment of heart disease. Patients with end stage heart failure fall into stage D of the ABCD classification of the American College of Cardiology (ACC)/American Heart Association (AHA), and class III-IV of the New York Heart Association (NYHA) functional classification. These patients are characterized by advanced structural heart disease and pronounced symptoms of heart failure at rest or upon minimal physical exertion, despite maximal medical treatment according to current guidelines. This patient population has a one-year mortality rate of approximately fifty percent and requires special therapeutic interventions.

Treatment of end stage heart failure may include implant of a mechanical circulatory support device (e.g., a ventricular assist device, such as a left ventricular assist device) to aid the heart in pumping blood to the body. A ventricular assist device may be used to sustain life until a heart transplant procedure may be performed (i.e., as a bridge to transplant), as a permanent solution to reduce the symptoms of heart disease (i.e., destination therapy), or as a temporary measure to treat a reversible condition (such as, e.g., myocarditis). Though ventricular assist devices may be effective in the treatment or management of symptoms of heart failure, ventricular assist devices may be susceptible to adverse incidents, including, but not limited to, pump thrombosis.

Ventricular assist device pump thrombosis may be characterized as a partial or complete blockage of the flow of blood in or near the ventricular assist device. For example, a blockage may occur in the inflow cannula, such as near an inflow valve; in the pump body, such as a rotor, impeller, or stators; or in the outflow graft, such as near an outflow valve. The causes of pump thrombosis may be classified as either pump-related, patient-related, or management-related. Pump-related causes of pump thrombosis may include, e.g., heat generated by moving parts or outflow graft kinks. Patient-related causes of pump thrombosis are factors that render patient more likely to have thrombotic complications, e.g., atrial fibrillation, infection, or preexisting conditions. Management-related causes of pump thrombosis are due to surgical or medical protocol choices, e.g., implantation techniques, extent of anticoagulation, or low pump flow due to a low speed setting.

Pump thrombosis may be classified as suspected pump thrombus or confirmed pump thrombus. In suspected pump thrombus, the clinical patient condition, such as hemolytic urine, or pump parameters, such as power draw, may suggest thrombus on any of the blood-contacting surfaces of the ventricular assist device. Confirmation of pump thrombus is typically done by visual inspection (e.g., during device exchange, transplantation, autopsy), evaluation of radiographic evidence, or by detecting absence or reduction of Doppler inflow or outflow signals, or another measure of blood flow.

SUMMARY

The disclosure describes systems and techniques for detection of pump thrombosis in mechanical circulatory support (MCS) devices. During operation, MCS devices produce a mechanical wave. In some examples, the mechanical wave includes an acoustic wave or a vibration. The mechanical wave defines a wave spectrum that includes a plurality of frequency peaks. Each respective frequency peak of the plurality of frequency peaks is produced by at least one of the turning of the rotor (e.g., impeller) of the MCS device, the rotor blades or flow channels passing the outflow cannula, peaks of other origin (e.g., electrical interference), and harmonics thereof. When a thrombus forms in or near the MCS device, one or more frequency peaks of the plurality of frequency peaks may change. By detecting a change in the mechanical wave, such as a change in one or more frequency peaks of the mechanical wave spectrum, or another change in the mechanical wave spectrum, the described systems and techniques detect pump thrombus of the MCS device.

In some examples, the disclosure describes a pump thrombosis detection system that includes a transducer and processing circuitry. The transducer is configured to generate a signal representative of a mechanical wave from a mechanical circulatory support device. The processing circuitry is communicatively coupled to the transducer. The processing circuitry is configured to determine an indication of pump thrombosis based on the signal and, based on the indication of pump thrombosis, control the pump thrombosis detection system to at least one of generate an alert or initiate an intervention.

In some examples, the disclosure describes a pump thrombosis detection system that includes a transducer, processing circuitry, and a user interface. The transducer is configured to generate a signal representative of a mechanical wave from a mechanical circulatory support device. The transducer is one of within or coupled to an implantable medical device remote from the mechanical circulatory support device. The processing circuitry is communicatively coupled to the transducer. The processing circuitry is configured to identify at least one portion of the signal representative of at least one harmonic of the mechanical wave and determine an indication of pump thrombosis based on the at least one portion. The user interface is communicatively coupled to the processing circuitry. The user interface is configured to alert a user of the indication of pump thrombosis.

In some examples, the disclosure describes a method for detection of pump thrombosis that includes receiving, by processing circuitry communicatively coupled to a transducer, a signal representative of a mechanical wave generated by a mechanical circulatory support device. The method also includes determining, by the processing circuitry, an indication of pump thrombosis based on the signal. The method also includes, based on the indication of the pump thrombosis, at least one of alerting, by a user interface communicatively coupled to the processing circuitry, a user of the indication of pump thrombosis or initiating an intervention.

In some examples, the disclosure describes a system for detection of pump thrombosis that includes means for receiving, by processing circuitry communicatively coupled to a transducer, a signal representative of a mechanical wave generated by a mechanical circulatory support device. The system also includes means for determining, by the processing circuitry, an indication of pump thrombosis based on the signal. The system also includes means for, based on the indication of the pump thrombosis, at least one of alerting, by a user interface communicatively coupled to the processing circuitry, a user of the indication of pump thrombosis or initiating an intervention.

In some examples, the disclosure describes a computer-readable storage medium comprising instructions that, when executed by processing circuitry of a medical device system, cause the processing circuitry to receive, from a transducer communicatively coupled to processing circuitry, a signal representative of a mechanical wave generated by a mechanical circulatory support device. The computer-readable storage medium further comprises instructions that, when executed by processing circuitry of the medical device system, cause the processing circuitry to determine an indication of pump thrombosis based on the signal. The computer-readable storage medium further comprises instructions that, when executed by processing circuitry of the medical device system, cause the processing circuitry to, based on the indication of the pump thrombosis, at least one of alert, by a user interface communicatively coupled to the processing circuitry, a user of the indication of pump thrombosis or initiating an intervention.

The details of one or more aspects of the disclosure are set forth in the accompanying drawings and the description below. Other features, objects, and advantages of the disclosure will be apparent from the description and drawings, and from the claims.

DETAILED DESCRIPTION

Figure 1:
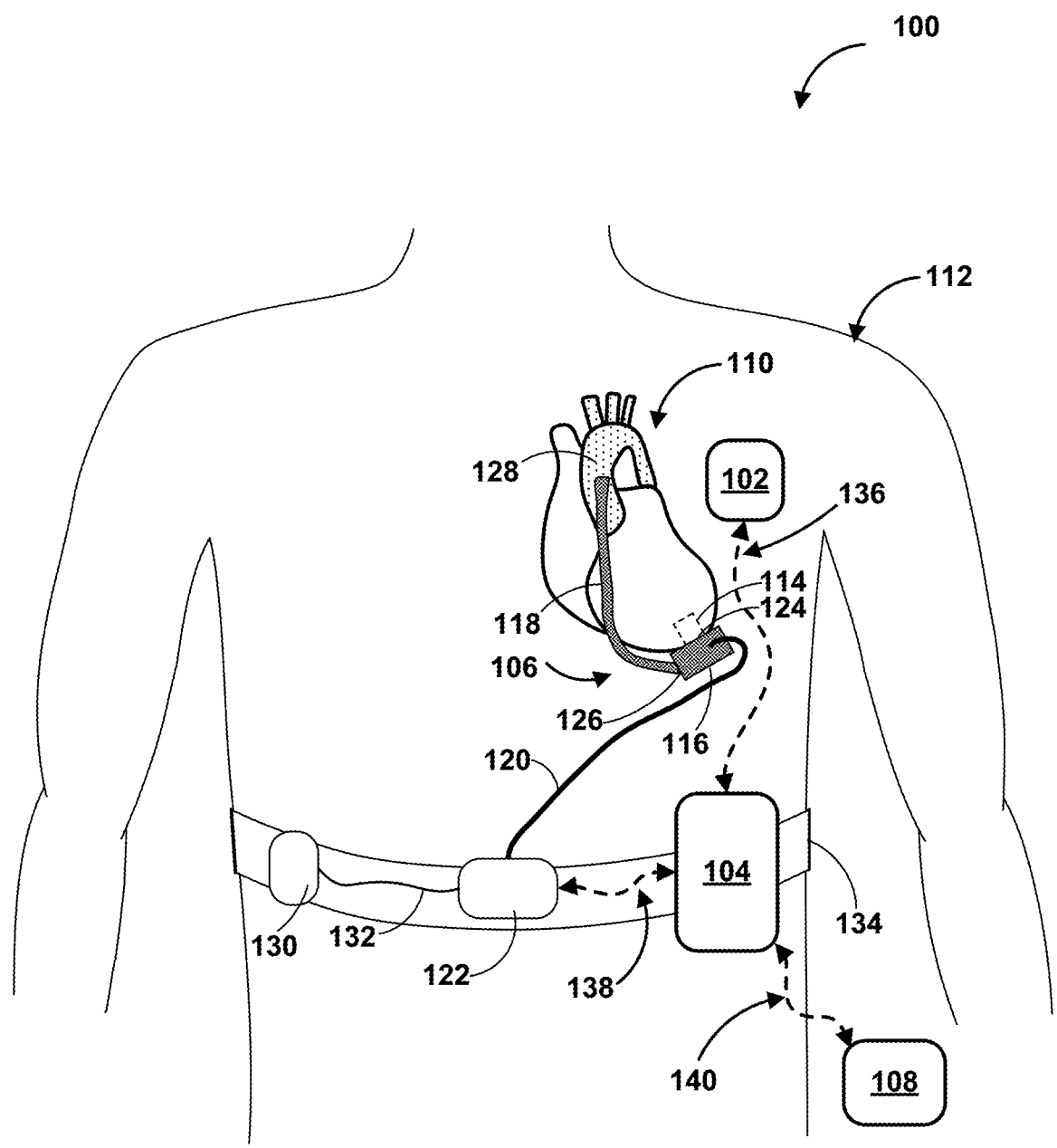
FIG. 1 is a conceptual and schematic diagram illustrating an example pump thrombosis detection system.

This disclosure describes systems and techniques for detection of pump thrombosis. Example systems include a transducer, processing circuitry, and a user interface. The transducer senses a mechanical wave from a mechanical circulatory support (MCS) device and generates a signal representative of the mechanical wave. The mechanical wave may include an acoustic wave or a vibration generated by an operation of the pump of the MCS device. The mechanical wave defines a wave spectrum (e.g., an acoustic spectrum) including a plurality of frequency peaks. Each respective frequency peak of the plurality of frequency peaks is produced by, for example, at least one of the turning of the rotor (e.g., impeller) of the pump, the rotor blades or flow channels of the pump passing the outflow cannula, peaks of other origin (e.g., electrical interference), and harmonics thereof. The amplitude or other characteristic(s) of one or more frequency peaks may change when a thrombus forms on, for example, at least one of a portion of the inflow cannula, the pump impeller, the pump casing, and the outflow cannula of the MCS device. The processing circuitry is communicatively coupled to the transducer and receives the signal. The processing circuitry determines an indication of pump thrombosis based on the signal. For example, the processing circuitry may determine a change in the amplitude of one or more harmonics of the signal. When an indication of pump thrombosis is detected, the processing circuitry controls the pump thrombosis detection system to generate an alert or initiate an intervention. In some examples, the processing circuitry may cause a user interface communicatively coupled to the processing circuitry to alert a user, such as, for example, the patient in which the MCS device is implanted, a caregiver, a clinician, or a remote server system (e.g., pump thrombosis detection platform), of the indication of pump thrombosis. In some examples, the processing circuitry may adjust an operational state of the MCS device (e.g., a pump speed or pulse the pump on and off) to breakup or dislodge the thrombus. In some examples, the processing circuitry may control a drug delivery device to delivery a thrombolytic agent to the pump to breakup or dislodge the thrombus. One or more of the transducer, processing circuitry, the user interface, and the drug delivery device may include implantable or wearable devices that allow the user to remain ambulatory while monitoring the CMS device for pump thrombosis. By using mechanical waves from the MCS device to detect pump thrombosis in an ambulatory patient, the systems and methods described herein may improve patient comfort, enable more accurate detection of pump thrombosis, earlier detection of pump thrombosis, or both compared to other systems and methods for detecting pump thrombosis. By generating an alert or initiating an intervention, the systems and methods described herein may reduce occurrences of MCS device replacement surgery or improve patient mortality due to pump thrombosis compared to other systems and methods.

FIG. 1 is a conceptual and schematic diagram illustrating an example pump thrombosis detection system 100. Pump thrombosis detection system 100 includes a transducer 102, a computing device 104, and user interface 108. Pump thrombosis detection system 100 is configured to detect pump thrombosis in MCS device 106 that is fluidically coupled to the heart 110 of patient 112. Although shown in FIG. 1 as two separate devices, in other examples, one or more of transducer 102, computing device 104, and user interface 108 may be included in the same device. Transducer 102, computing device 104, and user interface 108 are portable, e.g., able to be carried on or implanted in patient 112, to enable patient 112 to remain ambulatory while using pump thrombosis detection system 100.

MCS device 106 includes inflow cannula 114, pump 116, outflow cannula 118, and driveline 120. In some examples, MCS device 106 may be the same or substantially similar to the sealless rotary blood pump as described in U.S. Pat. No. 6,688,861 B2 by Wampler, titled SEALLESS ROTARY BLOOD PUMP, the contents of which are incorporated by reference herein in its entirety. In some examples, inflow cannula 114 may be the same or substantially similar to the conduit device as described in U.S. Pat. No. 8,870,739 B2 by LaRose et al., titled CONDUIT DEVICE FOR USE WITH A VENTRICULAR ASSIST DEVICE, the contents of which are incorporated by reference herein in its entirety. A first end of inflow cannula 114 may be fluidically coupled to inlet 124 of pump 116 and a second end of inflow cannula 114 may be grafted to heart 110, e.g., the left ventricle of heart 110. In some examples, the second end of inflow cannula 114 may connect to a ventricular connector, such as described in U.S. Pat. No. 8,403,823 B2 by Yu et al., titled VENTRICULAR CONNECTOR, the contents of which are incorporated by reference herein in its entirety. A first end of outflow cannula 118 is fluidically coupled to outlet 126 of pump 116, and a second end of outflow cannula 118 is grafted or otherwise fluidically coupled to an artery of patient 112, e.g., aorta 128.

Pump 116 is configured to draw blood from a chamber of heart 110 and pump the blood to other portions of the body of patient 112. Pump 116 may include any suitable biocompatible pump such as, for example, an axial flow pump, a centrifugal pump, a diaphragm pump, a pulsatile pump, a peristaltic pump, a screw pump, or a scroll pump. In some examples, pump 116 may be the same or substantially similar to the blood pump as described in U.S. Pat. No. 7,699,586 B2 by LaRose et al., titled WIDE BLADE, AXIAL FLOW PUMP, the contents of which are incorporated by reference herein in its entirety. Pump 116 includes a motor powered by driveline 120. For example, driveline 120 may provide electrical and/or mechanical power to the motor of pump 116. The power supplied by driveline 120 is controlled by MCS controller 122. In some examples, MCS device 106 may be communicatively coupled to MCS controller 122 via driveline 120. For example, MCS device 106 may communicate data associate with an operation of MCS device 106 to MCS controller 122 via driveline 120. MCS controller 122 may be powered by one or more batteries 130, which may be separately housed from MCS controller 122 and electrically coupled to MCS controller 122 by power cord 132. In the illustrated example, MCS controller 112 and one or more batteries 130 are removably attached to a carrier 134. One or more batteries 130 and carrier 134 allow patient 112 to remain ambulatory while using MCS device 106.

In some examples, transducer 102 is one of within or coupled to an implantable medical device (IMD) that is remote from the MCS device 106. The IMD may include, but is not limited to, at least one of a pacemaker, an implantable cardioverter-defibrillator, or an insertable cardiac monitor. An exemplary insertable cardiac monitor, referred to as Reveal LINQ™, is commercially available from Medtronic Inc. located in Minneapolis, Minn. In some examples, transducer 102 may be within or coupled to a wearable device (e.g., an externally-wearable device) or other portable device, such as, for example, a mobile phone, patch, chest strap, or a Holter monitor. In examples in which transducer 102 is within or coupled to an IMD, biological tissue may separate transducer 102 and MCS device 106. Transducer 102 may be sufficiently close to MCS device 106 to sense a mechanical wave, e.g., an acoustic wave or a vibration, from MCS device 106 through biological tissue of patient 112. In examples in which transducer 102 is a wearable device or portable device, transducer 102 is configured to be at least temporarily positioned proximate to MCS device 106 to sense a mechanical wave from MCS device 106 through biological tissue of patient 112 and, in some examples, an interstitial space between a surface of the body of patient 112 and transducer 102. The interstitial space may include, for example, air or clothing.

Transducer 102 includes any suitable device for sensing the mechanical wave from MCS device 106 and converting the mechanical wave into a signal, e.g., an electrical signal, an optical signal, or a wireless signal. For example, transducer 102 may include an electromagnetic transducer, an electrostatic transducer, capacitive micromachined transducer, or a piezoelectric transducer. In this way, transducer 102 is configured to sense at least one of a pressure wave, a mechanical vibration, and an electrical field representative of a mechanical wave from MCS device 106.

Transducer 102 is communicatively coupled (e.g., connected) to computing device 104 via link 136. Link 136 includes any suitable wired connection or a wireless connection, or a combination of both. For example, transducer 102 may include a communications interface, such as an Ethernet card, a radio frequency transceiver, cellular transceiver, a Bluetooth® interface card, USB interface, or any other type of device that can send and receive information. Transducer 102 generates a signal (e.g., output) representative of a mechanical wave from MCS device 106 and may provide the signal to computing device 104 via link 136. In some examples, transducer 102 may be configured to condition the signal prior to providing the signal to computing device 104. Conditioning may include, but is not limited to, amplification, filtering, attenuation, isolation, and/or transformation such as Fast Fourier Transformation. In some examples, transducer 102 may provide an unconditioned signal to computing device 104, which may condition the signal in some examples.

Computing device 104 includes any suitable computing device, such as a smartphone, a computerized wearable device (e.g., a watch, eyewear, ring, or necklace), or a tablet. Computing device 104 may be a consumer device configured to perform the techniques of this disclosure executing program instructions, or may be a special purpose device provided by, for example, the manufacturer of MCS device 106. In some examples, computing device 104 and transducer 102 are two separate devices. In some examples, computing device 104 and transducer 102 are components of the same device.

The signal from transducer 102 is received by processing circuitry of computing device 104. The processing circuitry may receive a conditioned signal or an unconditioned signal from transducer 102. In some examples, the processing circuitry may condition (or further condition) the received signal, for example, as described above. The processing circuitry of computing device 104 (and/or processing circuitry of one or more other devices of system 100) determines an indication of pump thrombosis based on the signal. Computing device 104 may include a data storage to store one or more signals. By receiving one or more signals from transducer 102, determining an indication of pump thrombosis based on the one or more signals, and storing the one or more signals or an indication of pump thrombosis, computing device 104 (and/or one or more other devices of system 100) may enable pump thrombosis detection system 100 to detect pump thrombosis in pump 116, track indications of pump thrombosis in pump 116 over time, or both.

In some examples, computing device 104 is communicatively coupled (e.g., connected) to MCS controller 122 via link 138. Link 138 may be the same or similar to link 136 discussed above. In some examples, computing device 104 and MCS controller 122 may be part of the same device. In some examples, computing device 104 may control an operation of MCS device 106 via MCS controller 122. For example, computing device 104 may initiate an intervention. The intervention may include adjusting an operational state of MCS device 106. In some examples, the operational state of MCS device 106 includes a speed (e.g., revolutions per minute) of pump 116 or an on/off state of pump 116 (e.g., pulsing pump 116). In some examples, computing device 104 may receive from MCS controller 122 data associated with MCS device 106 (e.g., MCS data). MCS data includes, but is not limited to, the age and model type of one or more components of MCS device 106, the age and usage of one or more batteries 130, the power consumption of pump 116, flow data associated with blood flow through pump 116, MCS device 106 temperature, revolutions per minute of pump 116 or the motor, and user input. In some examples, the MCS data is associated with pump thrombosis. In some examples, the MSC data may include data determined by the methods of characterizing divergence of a monitored flow rate of blood through an implantable blood pump and/or predicting an adverse event based on flow rate data from an implantable blood pump as described in United States Patent Application Publication Number 2017/0119256 A1 by Demou et al., titled METHODS AND SYSTEMS FOR ADVERSE EVENT PREDICTION USING PUMP OPERATING DATA, the contents of which are incorporated by reference herein in its entirety. For example, pump thrombosis may be associated with one or more of a decrease in pump 116 flowrate (e.g., pump output), an increase in power consumption by pump 116, or an indication of hemolysis (e.g., via user input).

In some examples, the MCS data is received by processing circuitry of computing device 104. The processing circuitry of computing device 104 (and/or processing circuitry of one or more other devices of system 100) determines an indication of pump thrombosis based on the signal generated by transducer 102, the MCS data, or both. For example, the processing circuitry determines the indication of pump thrombosis based on the signal and the MCS data. In some examples, the processing circuitry determines the indication of pump thrombosis based on the signal and confirms the determination of the indication of pump thrombosis based on the MCS data. In some examples, the processing circuitry determines the indication of pump thrombosis based on the MCS data and confirms the determination of the indication of pump thrombosis based on the signal. Computing device 104 may include a data storage to store the MCS data. By receiving MCS data from MCS controller 122; determining an indication of pump thrombosis based on the one or more signals, the MCS data, or both; and storing the MCS data or an indication of pump thrombosis, computing device 104 (and/or one or more other devices of system 100) enables pump thrombosis detection system 100 to detect pump thrombosis in pump 116, track MCS data over time, or both.

Additionally or alternatively, computing device 104, MCS controller 122, or both may be communicatively coupled (e.g., connected) to one or more additional cardiovascular system monitoring devices via a link, as discussed above. Cardiovascular system monitoring devices include, but are not limited to, pulse monitoring devices, blood oxygenation monitoring devices, blood pressure monitoring devices, prothrombin time monitoring devices, and user input. Computing device 104 receives from the one or more additional cardiovascular system monitoring devices data associated with MCS device 106 (e.g., auxiliary cardiovascular data). In some examples, the auxiliary cardiovascular data is associated with pump thrombosis. For example, pump thrombosis may be associated with one or more of a decrease in blood pressure, a decrease in blood oxygenation, an increase in power consumption by pump 116, or an indication of hemolysis (e.g., via user input).

In some examples, the auxiliary cardiovascular data is received by processing circuitry of computing device 104. The processing circuitry of computing device 104 determines an indication of pump thrombosis or confirm a determined indication of pump thrombosis based on the auxiliary cardiovascular and one or more signal, the MCS data, or both. By receiving auxiliary cardiovascular data; determining an indication of pump thrombosis based on the auxiliary cardiovascular and one or more signals, the MCS data, or both; and storing the auxiliary cardiovascular or an indication of pump thrombosis, computing device 104 enables pump thrombosis detection system 100 to detect pump thrombosis in pump 116, track auxiliary cardiovascular data over time, or both.

Computing device 104 is communicatively coupled (e.g., connected) to a user interface 108 via link 140. Link 140 is the same as link 136, as discussed above. User interface 108 includes a graphical user interface (GUI), a display, a keyboard, a touchscreen, a speaker, a microphone, a gyroscope, an accelerometer, a vibration motor, or the like. Computing device 104 includes one or more output components that generate tactile output, audio output, video output, or the like that is received by user interface 108 to communicate information to a user (e.g., patient 112, a caregiver, or a clinician) or another entity, such as a remote server system. In this way, user interface 108 may notify a user of an indication of pump thrombosis. As one example, user interface 108 receives an indication of pump thrombosis from computing device 104 and causes user interface 108 to generate an alert representative of the indication of pump thrombosis. The alert may be any type of information understandable by a human or machine, such as a user or another entity. For example, the alert may include information representative of the indication of pump thrombosis displayed on a display of user interface 108. In some examples, the display of user interface 108 may include a mobile device of the user and the information representative of the indication of pump thrombosis may be a text, email, push notification, or web application notification. Similarly, computing device 104 includes one or more input components that receive tactile input, kinetic input, audio input, optical input, or the like from a user or another entity via user interface 108. In this way, user interface 108 may receive user input from a user and send user input to computing device 104. For example, a user may provide user input to user interface 108, which communicates the user input to computing device 104. The user input (e.g., user data) includes, for example, at least one of information associated with an indication of pump thrombosis, information associated MCS data, and information associated with auxiliary cardiovascular data. By communicatively coupling output components and input components of computing device 104 to user interface 108, user (or another entity) may interact with computing device 104.

In some examples, computing device 104 is communicatively coupled (e.g., connected) to a drug delivery device (not shown in FIG. 1 for clarity). For example, the drug delivery device may be communicatively coupled to computing device 104 via a link, as discussed above. The drug delivery device may include any suitable drug delivery device for delivering a drug intervention to patient 112. The intervention may include a thrombolytic agent delivered to MCS device 106, such as pump 116. The thrombolytic agent may include any one or more suitable thrombolytic agent, such as, for example, urokinase, streptokinase, tissue plasminogen activator (TPA), and/or tenecteplase (TNK). In some examples, MCS device 106 may be configured to receive a drug intervention from a clinician. For example, a clinician may deliver a thrombolytic agent to MCS device, such as pump 116, via a drug delivery port. In this way, pump thrombosis detection system 100 may be configured to provide an intervention to patient 112.

Figure 2:
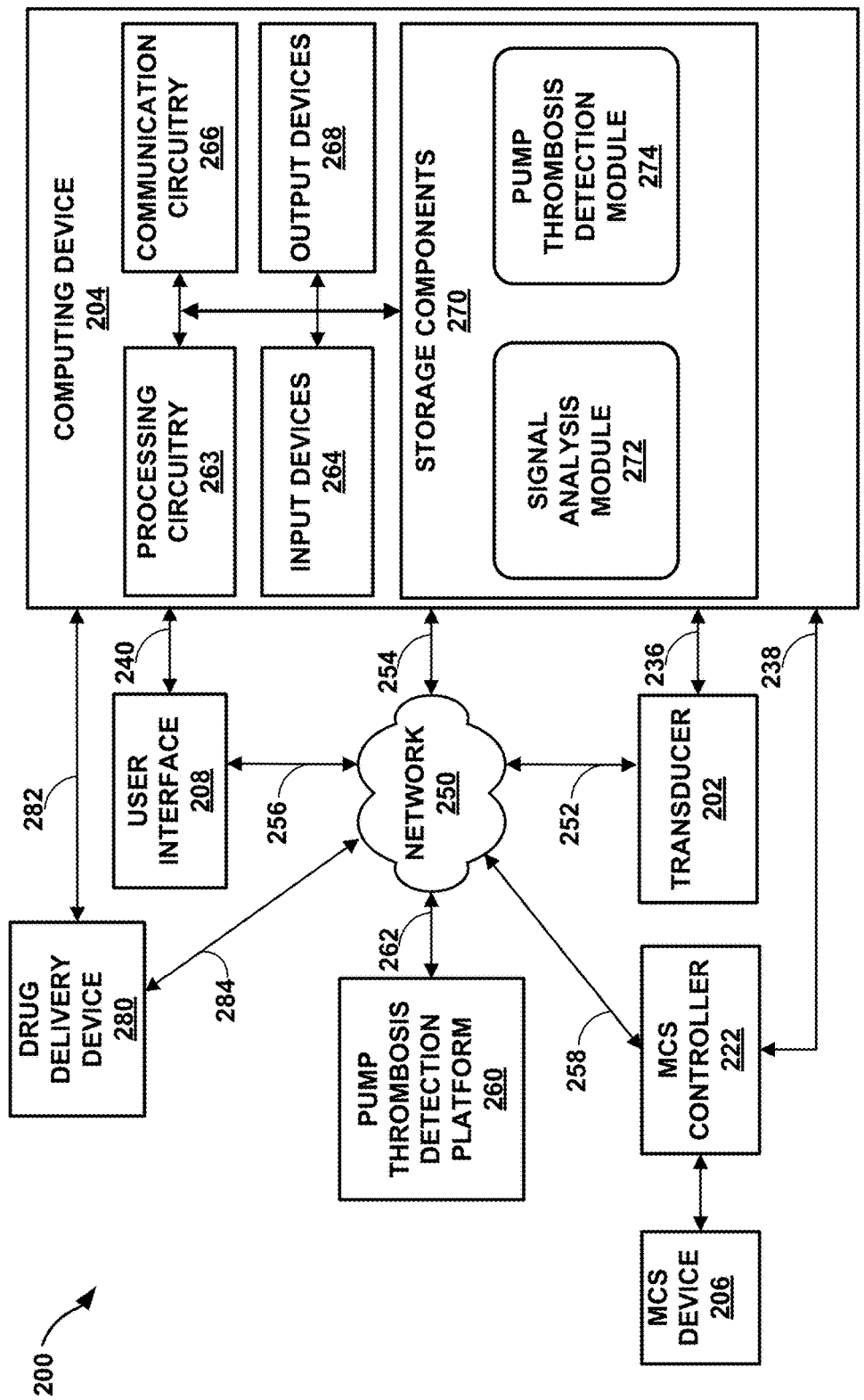
FIG. 2 is a functional block diagram illustrating an example configuration of a pump thrombosis detection system.

FIG. 2 is a functional block diagram illustrating an example configuration of a pump thrombosis detection system 200. Pump thrombosis detection system 200 may be the same or substantially similar to pump thrombosis detection system 100 of FIG. 1 except for the differences described herein. For example, like pump thrombosis detection system 100, pump thrombosis detection system 200 includes a transducer 202, a computing device 204, a user interface 208, a MCS device 206, and a MCS controller 222.

As shown in FIG. 2, transducer 202, computing device 204, user interface 208, and MCS controller 222 are optionally communicatively coupled to network 250. In some examples, fewer components (e.g., only computing device 204) may be coupled to network 250. Network 250 represents any public or private communication network, for instance, based on Bluetooth, WiFi®, a proprietary protocol for communicating with IMDs, or other types of networks for transmitting data between computing systems, servers, and computing devices, both implanted within and external to a patient. Transducer device 202, computing device 204, user interface 208, and MCS controller 222 may each be operatively coupled to network 250 using respective network links 252, 254, 256, and 258. Network links 252, 254, 256, and 258 may be any type of network connections, such as wired or wireless connections as discussed above. Network 250 may provide selected devices, such as transducer device 202, computing device 204, user interface 208, and MCS controller 222 with access to the Internet, and may allow transducer device 202, computing device 204, user interface 208, and MCS controller 222 to communicate with each other. For example, rather than communicating via link 236, transducer 202 and computing device 204 may communicate via network links 252 and 254. Similarly, rather than communicating via link 238, computing device 204 and MCS controller 222 may communicate via network links 254 and 258. Similarly, rather than communicating via link 240, computing device 204 and user interface 208 may communicate via network links 254 and 256.

In some examples, the network is operatively coupled to a pump thrombosis detection platform 260 via network link 262. Network link 262 may be the same or substantially similar to network links 252, 254, 256, and 258 discussed above. For example, computing device 204 may communicate with pump thrombosis detection platform 260 via network link 262.

In some examples, computing device 204 may send data to pump thrombosis detection platform 260, receive data from pump thrombosis detection platform 260, or both via network 250. For example, computing device 204 may send at least one of one or more signals (e.g., conditioned or unconditioned signals from transducer 204), indications of pump thrombosis, MCS data, auxiliary cardiovascular data, and user data to pump thrombosis detection platform 260. In some examples, pump thrombosis detection platform 260 may store data received from a plurality of patients as captured by, for instance, at least one of one or more signals, indications of pump thrombosis, MCS data, auxiliary cardiovascular data, and user data received from a plurality of computing devices (e.g., computing device 204). Pump thrombosis detection platform 260 may analyze at least one of one or more signals, indications of pump thrombosis, MCS data, auxiliary cardiovascular data, and user data to determine an indication of pump thrombosis. In this way, pump thrombosis detection platform 260 may perform one or more functions discussed herein with respect to computing device 204. Additionally, or alternatively, pump thrombosis detection platform 260 may analyze at least one of one or more signals, indications of pump thrombosis, MCS data, auxiliary cardiovascular data, and user data to determine one or more factors attributable to indications of pump thrombosis. For example, pump thrombosis detection platform 260 may analyze one or more signals from a plurality of computing devices (e.g., each respective computing device associated with a respective patient) to determine threshold signal values indicative of pump thrombosis. In this way, pump thrombosis detection platform 260 may be configured to improve the accuracy of a determination of pump thrombosis.

Computing device 204 also may receive data from pump thrombosis detection platform 260 including, for example, stored signals, stored indications of pump thrombosis, stored user data, notification data (e.g., regarding indications of pump thrombosis), algorithm data (e.g., to update or modify algorithms used by computing device 204 to determine an indication of pump thrombosis), and the like. In this way, pump thrombosis detection system 200 may collect and analyze one or more signals, indications of pump thrombosis, MCS data, auxiliary cardiovascular data, and user data from at least one computing device 204 to notify the at least one patient (e.g., via user interface 208) of an indication of pump thrombosis or information relevant to the user (e.g., whether a pump model, a pump of an identified age range, a pump with an identified operational history, a pump used in a patient with an identified medical history or treatment history, or the like may be likely to experience pump thrombosis).

Pump thrombosis detection system 200 includes a drug delivery device 280. Drug delivery device 280 may include any suitable drug delivery device for delivering an intervention to a patient. Drug delivery device may be communicatively coupled to computing device 204 via link 282. Link 282 may be the same as or substantially similar to links 236, 238, and 240, as discussed above. Additionally or alternatively, drug delivery device 280 may be operatively coupled to network 250 via network link 284. Network link 284 may be the same as or substantially similar to network links 252, 254, 256, and 258, as discussed above. For example, computing device 204 may communicate with drug delivery device 280 via network link 284.

Computing device 204 may control drug delivery device 280 to deliver an intervention to a patient. In some examples, computing device 204 may control drug delivery device 280 to deliver or increase a rate of delivery of a thrombolytic agent to MCS device 206, such as into a blood stream of a patient or directly to a component of MCS device 206. The thrombolytic agent may be configured to breakup (e.g., at least partially dissolve) or dislodge a thrombus from MCS device 206. In some examples, pump thrombosis detection platform may be configured to communicate with drug delivery device 280 via network 250 to control drug delivery device 280 to deliver the thrombolytic agent to MCS device 206. In this way, pump thrombosis detection system 200, for example, drug delivery device 280, may be configured to provide an intervention to a patient.

Although computing device 204 of FIG. 2 is shown separate from transducer 202, user interface 208, and MCS controller 222, in some examples, computing device 204 may include one or more of transducer 202, user interface 208, and MCS controller 222. For example, rather than being coupled by links, computing device 204 and user interface 208 may form an integrated device, such as a mobile phone or a wearable medical device monitor. In one example approach, computing device 204 includes processing circuitry 263, one or more one or more input devices 264, communications circuitry 266, one or more output devices 268, and one or more one or more storage components 270. In some examples, the one or more storage components 270 include signal analysis module 272 and pump thrombosis detection module 274. In some examples, computing device 204 may include additional components or fewer components than those illustrated in FIG. 2.

Processing circuitry 263 includes various type of hardware, including, but not limited to, microprocessors, controllers, digital signal processors (DSPs), application specific integrated circuits (ASICs), field-programmable gate arrays (FPGAs), or equivalent discrete or integrated logic circuitry, as well as combinations of such components. The term "processing circuitry" may generally refer to any of the foregoing logic circuitry, alone or in combination with other logic circuitry, or any other equivalent circuitry. Processing circuitry 363 represents hardware that can be configured to implement firmware and/or software that sets forth one or more of the algorithms described herein. For example, processing circuitry 263 are configured to implement functionality, process instructions, or both for execution within computing device 204 of processing instructions stored within one or more storage components 270, such as signal analysis module 272 and/or pump thrombosis detection module. In some examples, processing circuitry 263 includes processing circuitry of an IMD and/or other devices of system 200 (e.g., computing device 104 may be in one or more devices of system 200).

Computing device 204 also includes one or more input devices 264. Input devices 264, in some examples, are configured to receive input from a user through tactile, audio, or video sources. Examples of input devices 264 include user interface 208, a mouse, a button, a keyboard, a voice responsive system, video camera, microphone, touchscreen, or any other type of device for detecting a command from a user. In some example approaches, user interface 208 includes all input devices 264 employed by computing device 204.

Computing device 204 further includes communications circuitry 266. Computing device 204 may utilize communications circuitry 266 to communicate with external devices (e.g., transducer 202, MCS controller 222, user interface 208, and/or pump thrombosis detection platform 260) via one or more networks, such as one or more wired or wireless networks. Communications circuitry 266 may include a communications interface, such as an Ethernet card, a radio frequency transceiver, cellular transceiver, a Bluetooth® interface card, USB interface, or any other type of device that can send and receive information. In some examples, computing device 204 utilizes communications circuitry 266 to wirelessly communicate with an external device such as a remote server system (e.g., pump thrombosis detection platform 260).

Computing device 204 may further include one or more output devices 268. Output devices 246, in some examples, are configured to provide output to a user using, for example, audio, video or tactile media. For example, output devices 246 may include user interface 208, a sound card, a video graphics adapter card, or any other type of device for converting a signal into an appropriate form understandable to humans or machines. In some example approaches, user interface 208 includes all output devices 246 employed by computing device 204.

One or more storage components 270 may be configured to store information within computing device 204 during operation. One or more storage components 270, in some examples, include a computer-readable storage medium or computer-readable storage device. In some examples, one or more storage components 270 include a temporary memory, meaning that a primary purpose of one or more storage components 270 is not long-term storage. One or more storage components 270, in some examples, include a volatile memory, meaning that one or more storage components 270 does not maintain stored contents when power is not provided to one or more storage components 270. Examples of volatile memories include random access memories (RAM), dynamic random-access memories (DRAM), static random-access memories (SRAM), and other forms of volatile memories known in the art. In some examples, one or more storage components 270 are used to store program instructions for execution by processing circuitry 263. One or more storage components 270, in some examples, are used by software or applications running on computing device 204 to temporarily store information during program execution.

In some examples, one or more storage components 270 may further include one or more storage components 270 configured for longer-term storage of information. In some examples, one or more storage components 270 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

As noted above, computing device 204 also may include signal analysis module 272 and pump thrombosis detection module 274. Each of signal analysis module 272 and pump thrombosis detection module 274 may be implemented in various ways. For example, one or more of signal analysis module 272 and pump thrombosis detection module 274 may be implemented as an application or a part of an application executed by processing circuitry 263. In some examples, one or more of signal analysis module 272 and pump thrombosis detection module 274 may be implemented as part of a hardware unit of computing device 204 (e.g., as circuitry). In some examples, one or more of signal analysis module 272 and pump thrombosis detection module 274 may be implemented remotely on a remote serve system (e.g., pump thrombosis detection platform 260) as part of an application executed by one or more processors of the remote serve system or as a hardware unit of the remote serve system. Functions performed by one or more of signal analysis module 272 and pump thrombosis detection module 274 are explained below with reference to the example flow diagrams illustrated in FIGS. 5 and 6.

Figure 3:
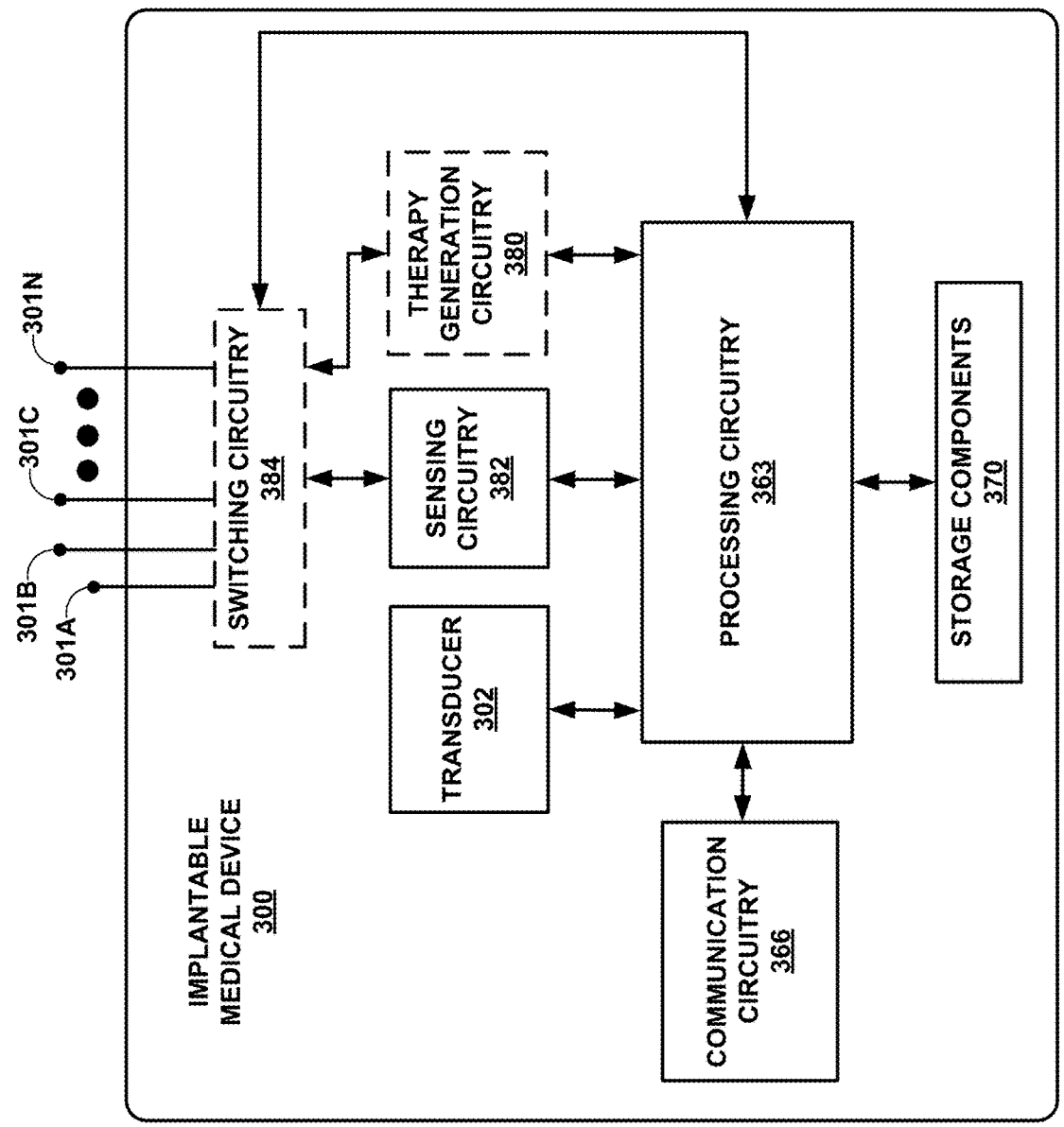
FIG. 3 is a functional block diagram illustrating an example configuration of an implantable medical device that includes a transducer.

FIG. 3 is a block diagram of an example configuration of an IMD 300 that includes a transducer 302. IMD 300 of FIG. 3 may, in various use case scenarios, represent an example of transducer 102 of FIG. 1 or transducer 202 of FIG. 2. IMD 300 includes two or more electrodes 301A-N (collectively "electrodes 301"), which may correspond to defibrillation electrodes, sensing electrodes, housing electrodes, or other electrodes of an IMD system, such as a pacemaker, an implantable cardioverter-defibrillator (ICD), insertable cardiac monitor (ICM), or a cardiac resynchronization therapy device.

IMD 300 includes processing circuitry 363 for controlling transducer 302, communication circuitry 366, storage components 370, sensing circuitry 382, and, optionally switching circuitry 384 and therapy generation circuitry 380. Dashed-line borders are used in FIG. 3 to show the optional nature of switching circuitry 384 and therapy generation circuitry 380. As one example, therapy generation circuitry 380 is indicated as optional because an example IMD 300 may include an ICM device, which do not deliver therapy. Switching circuitry 384 may include one or more switches, such as metal-oxide-semiconductor field-effect transistors (MOSFETs) or bipolar transistors. Processing circuitry 363 may control switching circuitry 384 to connect selected groupings of electrodes 301 to sensing circuitry 382 (or therapy generation circuitry 380) to sense one or more physiological electrical signals (or deliver therapy). Switching circuitry 384 is indicated as optional because, in some examples, IMD is configured such that switching between electrodes 301 is not necessary.

Transducer 302 may be the same or substantially similar to transducer 102 of FIG. 1 and/or transducer 202 of FIG. 2. For example, transducer 302 is sufficiently close to an MCS device (e.g., MCS device 106 and/or 206) to sense a mechanical wave from the MCS device through biological tissue of a patient. As discussed above, transducer 302 includes any suitable device (e.g., electromagnetic transducer, an electrostatic transducer, capacitive micromachined transducer, or a piezoelectric transducer) for sensing the mechanical wave from an MCS device and converting the mechanical wave into a signal that may be used by processing circuitry 363. As shown in FIG. 3, transducer 302 may be within IMD 300. In some examples, transducer 302 may be external from and communicatively coupled to IMD 300.

Sensing circuitry 382 is configured to receive cardiac electrical signals from selected combinations of two or more electrodes 301, and sense cardiac events attendant to depolarization and repolarization of cardiac tissue. Sensing circuitry 382 may include one or more sensing channels, each of which may be selectively coupled to respective combinations of electrodes 301 to detect electrical activity of a particular chamber of heart 112, e.g., one or more atrial and/or ventricular sensing channels. Each sensing channel may be configured to amplify, filter and rectify the cardiac electrical signal received from selected electrodes coupled to the respective sensing channel to detect cardiac events, e.g., P-wave and R-waves. The resulting cardiac electrical signal may be used to detect a cardiac event, e.g., when the cardiac electrical signal crosses a sensing threshold. Sensing circuitry 382 may output an indication to processing circuitry 363 in response to sensing a cardiac event in a chamber of interest, e.g., a P-wave or R-wave. Indications of detected R-waves may be used by processing circuitry 363 for detecting ventricular arrhythmia episodes, and indications of detected P-waves may be used by processing circuitry 363 for detecting atrial arrhythmia episodes. Sensing circuitry 382 may also pass one or more digitized EGM signals to processing circuitry 363 for analysis, e.g., for use in cardiac rhythm discrimination and/or for morphological analysis.

Communication circuitry 366 may include circuitry for generating and modulating, and in some cases receiving and demodulating, continuous and/or pulsatile communication waveforms. Communication circuitry 366 may be configured to transmit and/or receive one or both of RF signals via an antenna (not shown) or tissue conduction communication (TCC) signals via electrodes 301. Although not shown in FIG. 3, communication circuitry 366 may be coupled to a selected two or more electrodes 301 via switching circuitry 384 for TCC.

In some examples, processing circuitry 363 may control switching circuitry 384 to connect electrodes 301 to therapy generation circuitry 380 to deliver a therapy pulse, such as a pacing, cardioversion, or defibrillation pulse to the heart. Therapy generation circuitry 380 is electrically coupleable to electrodes 301 and configured to generate and deliver electrical therapy to heart 110 via selected combinations of electrodes 301. Therapy generation circuitry 380 may include charging circuitry, and one or more charge storage devices, such as one or more high voltage capacitors and/or one or more low voltage capacitors. Switching circuitry 384 may control when the capacitor(s) are discharged to selected combinations of electrodes 301. Therapy generation circuitry 380 and/or processing circuitry 363 may control the frequency, amplitude, and other characteristics of the therapy pulses. Therapy generation circuitry 380 may deliver the therapy pulses to electrodes 301 when switching circuitry 384 connects therapy generation circuitry 380 to electrodes 301.

Processing circuitry 363 may control switching circuitry 384 by sending control signals to the control terminals of one or more switches of switching circuitry 384. The control signals may control whether the switches of switching circuitry 384 conduct electricity between the load terminals of the switches. If switching circuitry 384 includes MOSFET switches, the control terminals may include gate terminals, and the load terminals may include drain terminals and source terminals.

Processing circuitry 363 may be the same as or substantially similar to processing circuitry 263 discussed above with respect to FIG. 2. For example, processing circuitry 363 may be configured to implement functionality, process instructions, or both for execution within IMD 300 of processing instructions stored within one or more storage components 370. Storage components 370 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Figure 4:
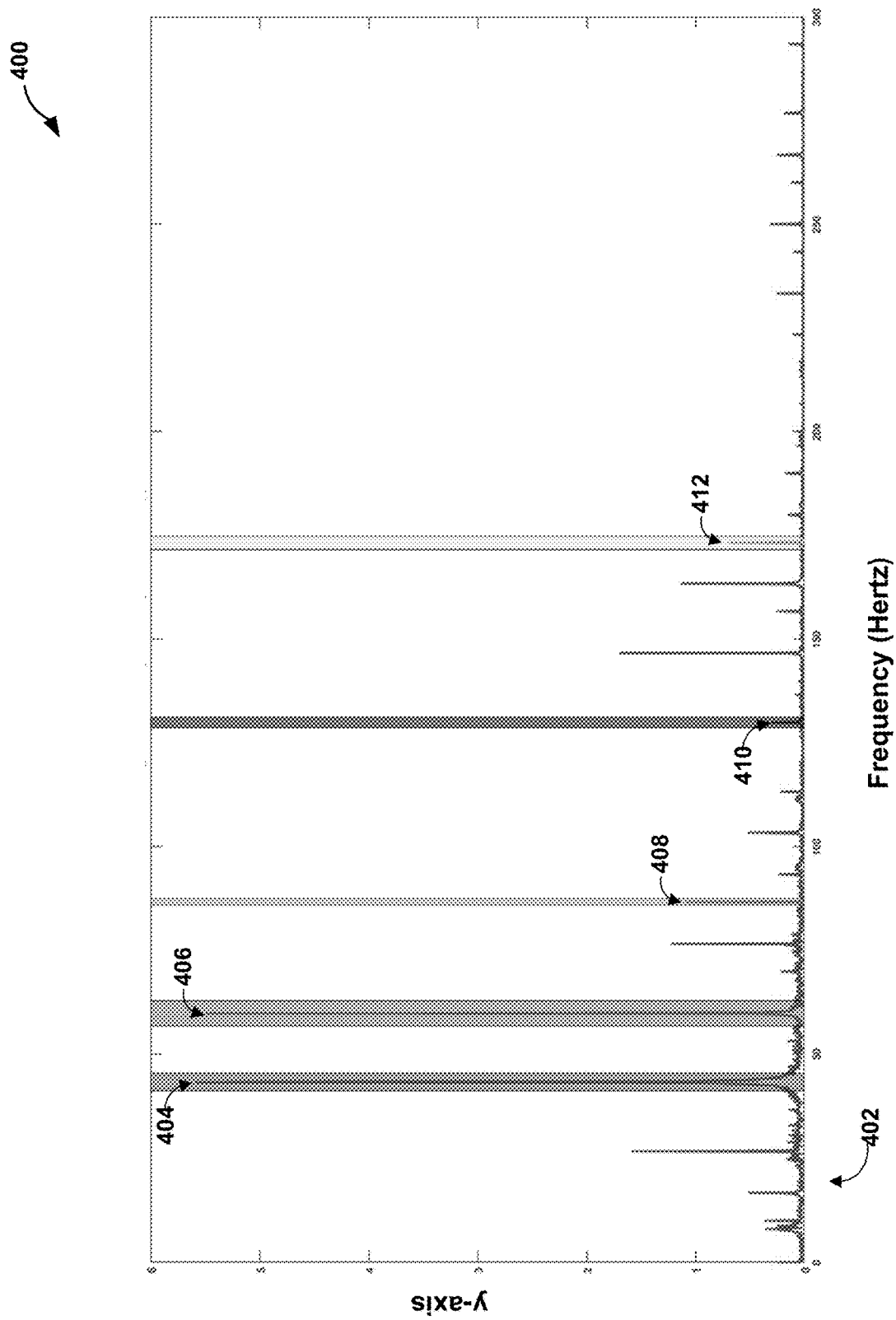
FIG. 4 is a conceptual diagram illustrating an example signal representative of a mechanical wave from a mechanical circulatory support device with pump thrombosis.

FIG. 4 is a conceptual diagram 400 illustrating an example signal 402 representative of a mechanical wave from an MCS device (e.g., MCS device 106 or 206) with pump thrombosis. With respect to diagram 400, the x-axis of includes frequency in Hertz of signal 402 and the y-axis includes a magnitude of the Fourier spectrum of signal 402. In some examples, signal 402 may be represented in diagrams with different units and/or different functions may be applied to signal 402. For example, signal 402 may be normalized relative to a selected harmonic of signal 402, such as a fourth harmonic of signal 402, or a frequency that is unrelated to the pump mechanics (e.g., the base frequency or harmonics thereof). Signal 402 includes features 404, 406, 408, 410, and 412. Features 404, 406, 408, 410, and 412 may include features that are unique to the mechanical wave from the MCS device having particular operation conditions, such as pump speed and presence of a thrombus in at least a portion of the MCS device. For example, feature 404 includes a rotor frequency. The rotor frequency includes a frequency peaks produced by the turning of the rotor (e.g., impeller) of the MCS device. Feature 402 includes electrical interference. The electrical interference may be due to a frequency of the power supplied to drive the pump of the MCS device (e.g., 60 Hertz). Features 408, 410, and 412 include, respectively, the second harmonic, third harmonic, and fourth harmonic of the rotor frequency (feature 404). In some examples, a first operational state of the MCS device may result in a respective harmonic having a first amplitude and/or a first frequency range, and a second operational state of the MCS device may result in a respective harmonic having a second, different amplitude and/or a second different frequency range. The operational state of the MCS device may include a speed of the pump (e.g., revolutions per minute) of the MCS device and/or the presence of a thrombus in at least a portion of the MCS device.

In some examples, a respective harmonic may have a first relatively smaller amplitude when no thrombus is present in the MCS device, and a second relatively larger amplitude when a thrombus is present in the MCS device. For example, third harmonic (feature 410) may be negligible compared to the adjacent signal (e.g., the portion of the signal within about 10 Hz of the frequency range including the third harmonic) when no thrombus is present in the MCS device. As shown in FIG. 4, third harmonic (feature 410) includes a detectable amplitude (e.g., compared to other features 408 and 412) when a thrombus is present in the MCS device. By detecting a change in an amplitude of the pump thrombosis detection system (e.g., pump thrombosis detection system 100 or 200) may detect the presence of a thrombus in the MCS device.

In some examples, a first operational state of the MCS device includes a relatively faster pump speed may result in a respective harmonic having a respective first frequency range, and a second operational state of the MCS device includes a relatively slower pump speed (e.g., relative to the first operational state) may result in the respective harmonic having a respective second, different frequency range (e.g., relatively less than the respective first frequency range). In some examples, the operational state of the MCS device, e.g., pump speed, may be controlled to identify first features related to the operational state (e.g., features 404, 408, 410, and 412) and second features that are unrelated to the operational state (e.g., feature 406). In this way, the operational state of the MCS device may be controlled to identify features in a signal that are unrelated to the MCS device (e.g., noise in the signal). By identifying features that are unrelated to the MCS device, a pump thrombosis detection algorithm may be configured to reduce or cancel noise in a signal.

Figure 5:
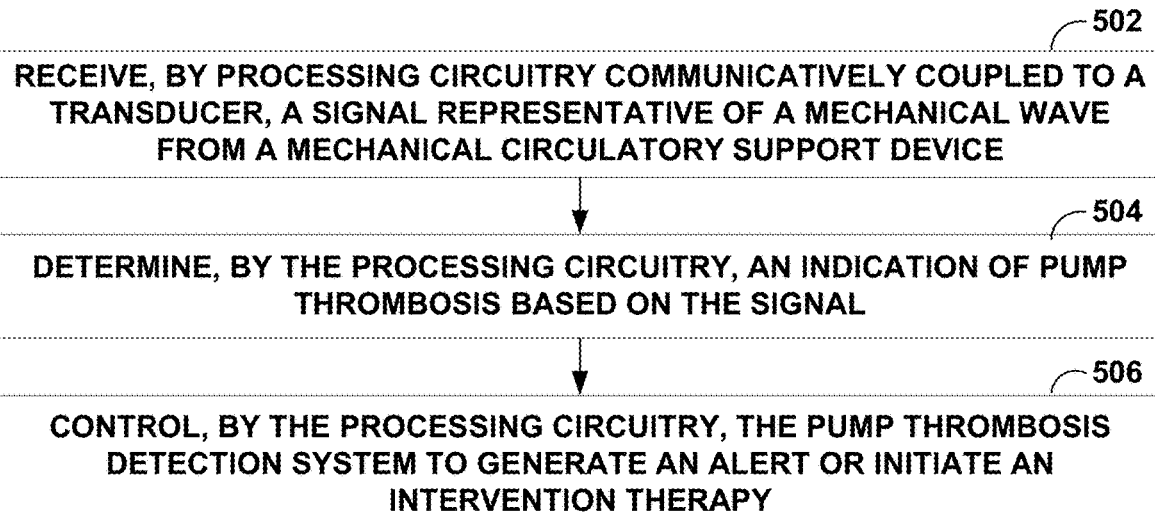
FIG. 5 is a flow diagram illustrating an example method of detecting pump thrombosis.

FIG. 5 is a flow diagram illustrating an example method of detecting pump thrombosis. Although the technique of FIG. 5 will be described with respect to pump thrombosis detection systems 100 and 200 of FIGS. 1 and 2, in some examples, the technique of FIG. 5 may be performed using a different system. Additionally, pump thrombosis detection systems 100 and 200 may perform other techniques for determining an indication of pump thrombosis, alerting a user of an indication of pump thrombosis, or both.

The technique illustrated in FIG. 5 includes receiving, by processing circuitry 263 communicatively coupled to transducer 202, a signal representative of a mechanical wave from by a MCS device 206 (502). The signal includes frequency and amplitude data representative of the mechanical wave (e.g., an acoustic wave or vibration). In some examples, the signal may include different or additional data representative of the mechanical wave. The mechanical wave may include at least one feature indicative of pump thrombosis. Processing circuitry 263 may receive the signal directly from transducer 202 or via an intermediate component, such as MCS controller 222, user interface 208, and/or pump thrombosis detection platform 260.

After receiving the signal (502), the technique illustrated in FIG. 5 includes determining, by processing circuitry 263, for example, pump thrombosis detection module 274, an indication of pump thrombosis based on the signal (504). In some examples, uses one or more signal processing algorithms to identify features in the mechanical wave. The features may include, for example, the amplitude of the mechanical wave at one or more selected frequencies or ranges of frequencies (e.g., one or more harmonics).

After determining the indication of pump thrombosis (504), the technique illustrated in FIG. 5 includes alerting, by user interface 208 communicatively coupled to processing circuitry 263, a user of the indication of pump thrombosis (506). For example, as discussed above, user interface 208 may receive an indication of pump thrombosis from computing device 204, e.g., pump thrombosis detection module 274, and cause user interface 108 to generate an alert representative of the indication of pump thrombosis. As discussed above, the alert may be any type of information understandable by a human or machine, such as a user or another entity.

In another example approach, signals from transducer 202 are received by computing device 204 and forwarded to pump thrombosis detection platform 260 for analysis. In one such example approach, pump thrombosis detection platform 260 receives one or more signals from one or more computing devices 204, associates each signal with a user (e.g., patient 112) and determines, from each signal, characteristics of an indication of pump thrombosis. In some examples, pump thrombosis detection platform 260 also receives MCS data, auxiliary cardiovascular data, and/or user input, as discussed above. Pump thrombosis detection platform 260 may aggregate characteristics of an indication of pump thrombosis (and, in some examples, MCS data, auxiliary cardiovascular data, and/or user input) for a plurality of users. Pump thrombosis detection platform 260 may use the aggregated characteristics to modify one or more algorithms used to determine an indication of pump thrombosis. For example, pump thrombosis detection platform 260 may calculate, for each user, one or more parameters of one or more algorithms associated with determining an indication of pump thrombosis and may, in some instances, modify at least one parameter based on MCS data, auxiliary cardiovascular data, and/or user input to tune pump thrombosis detection to the individual user. In this way, the one or more modified algorithms may more accurately determine indications of pump thrombosis. Pump thrombosis detection platform 260 may communicate the one or more modified algorithms to the plurality of computing devices (e.g., computing device 204). The plurality of computing devices may update pump thrombosis detection module 274 based on the one or more modified algorithms. By aggregating characteristics of an indication of pump thrombosis for a plurality of users, pump thrombosis detection system 200 may modify algorithms used to detect pump thrombosis to enable earlier detection of pump thrombosis, more accurately detection of pump thrombosis, or both compared to pump thrombosis detection systems without the one or more modified algorithms.

Figure 6:
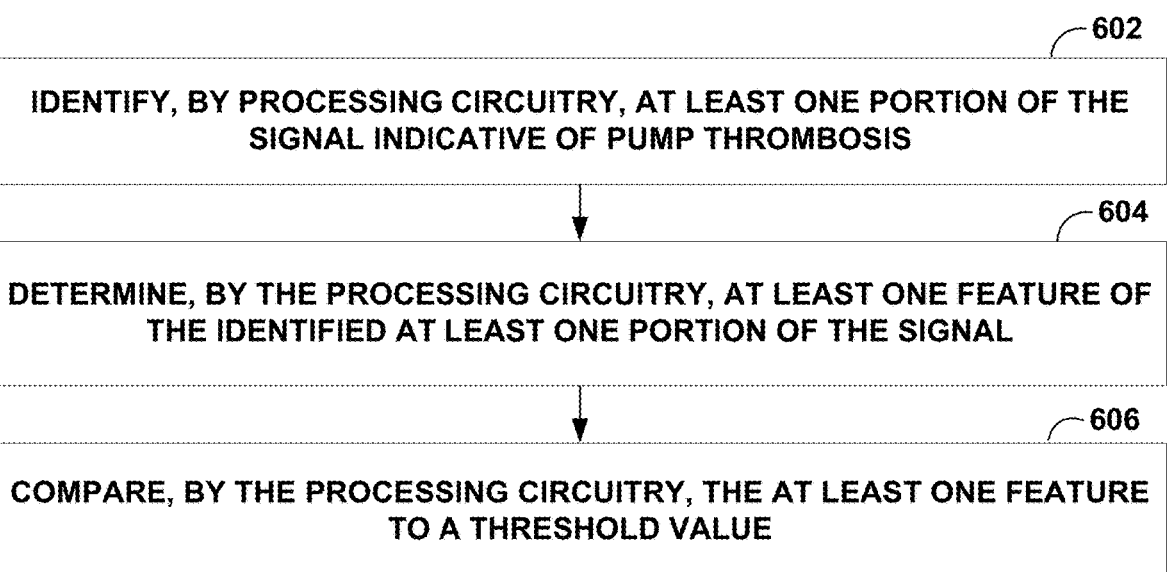
FIG. 6 is a flow diagram illustrating an example method of determining an indication of pump thrombosis based on a signal.

FIG. 6 is a flow diagram illustrating an example method of determining an indication of pump thrombosis based on a signal (e.g., step 504 of FIG. 5). As discussed above with respect to FIG. 5, processing circuitry 263 may use one or more signal processing algorithms to identify features in the mechanical wave. In some examples, the feature of the signal includes one or more harmonics of the mechanical wave. The technique illustrated in FIG. 6 includes identifying, by processing circuitry 263, for example, signal analysis module 272, at least one portion of the signal indicative of pump thrombosis (602). For example, the mechanical wave may include at least one of a basic frequency of the MCS device pump rotor and its harmonics and one or more frequencies associated with rotor blades passing the outlet cannula. As one example, a mechanical wave includes a basic frequency of the rotor (e.g., first harmonic or fundamental frequency associated with the turning of the rotor of the MCS device, and/or the rotor blades and/or flow channels passing the outflow cannula). The basic frequency of the rotor includes multiples of the basic frequency, e.g., a second harmonic, a third harmonic, a fourth harmonic, and the like. A four blade (or four flow channel) rotor may produce a frequency substantially equal to the fourth harmonic. In some examples, the at least one portion includes at least one harmonic of the mechanical wave. Processing circuitry 263 may identify a respective harmonic (e.g., the at least one portion of the signal representative of at least one harmonic of the mechanical wave) based on a dictionary of predicted harmonic range values or a dictionary of observed harmonic range values. The dictionary of predicted harmonic range values may include a plurality of harmonic range values predicted based on an operation of a MCS device (e.g., associated with revolutions per minute of the rotor or power usage of the pump). Similarly, the dictionary of observed harmonic range values may include a plurality of experimentally observed harmonic range values based on an operation of a MCS device. In some examples, the selected harmonic is the third harmonic. In some examples, the selected harmonic may be a harmonic different than the third harmonic or a plurality of harmonics. Identifying at least one portion of the signal indicative of pump thrombosis may increase the computing speed of computing device 204, reduce the processing power required to determine an indication of pump thrombosis, or both.

In some examples, identifying at least one portion of the signal indicative of pump thrombosis may optionally include cancelling noise in the signal. For example, after receiving a first signal, processing circuitry 263, may adjust the operational state (e.g., pump speed) of MCS device 206. After adjusting the operational state of MCS device 206, processing circuitry 263 may receive a second signal representative of the mechanical wave from MCS device 206 having the adjusted operational state. After receiving the second signal, processing circuitry 263, for example, signal analysis module 272, may compare the first signal and the second signal to identify features unrelated to MCS device 206 (e.g., noise). After identifying the noise, processing circuitry 263, for example, signal analysis module 272, may remove at least a portion of the noise from the first signal and/or the second signal. Removing the noise from the signal may increase the computing speed of computing device 204, reduce the processing power required to determine an indication of pump thrombosis, and/or increase the accuracy of the determination of pump thrombosis.

The technique illustrated in FIG. 6 also includes determining, by processing circuitry 263, for example, signal analysis module 272, at least one feature of the identified at least one portion of the signal (604). For example, the processing circuitry 263, e.g., signal analysis module 272, may determine a respective amplitude of the mechanical wave for the identified harmonic. In some examples, determining the respective amplitude of the mechanical wave for the identified harmonic includes normalizing the identified harmonic based on a different harmonic. For example, processing circuitry 263, e.g., signal analysis module 272, may normalize the amplitude of the third harmonic based on the amplitude of a different harmonic, such as the first harmonic, the second harmonic, or the fourth harmonic. In this way, processing circuitry 263, e.g., signal analysis module 272, may identify at least one portion of the signal representative of at least one harmonic of the mechanical wave, normalize at least one portion of the signal representative of at least one harmonic of the mechanical wave based on a different portion of the signal, or both.

The technique illustrated in FIG. 6 includes comparing, by processing circuitry 263, for example, pump thrombosis detection module 274, the at least one feature (of the identified at least one portion of the signal) to a threshold value (606). In some examples, processing circuitry 263, e.g., pump thrombosis detection module 274, compares the identified features to a dictionary of features. The dictionary of features may be stored by computing device 204, e.g., pump thrombosis detection module 274. In some examples, processing circuitry 263 may retrieve the dictionary of features, e.g., from pump thrombosis platform 260. In some examples, processing circuitry 263 may derived at least one feature of the dictionary of features from one or more signals. By comparing a feature of a signal to a dictionary of features, processing circuitry 263 may determine an indication of pump thrombosis based on the signal.

In examples in which processing circuitry 263 derives at least one feature of the dictionary of features, the derived feature may be based on a second signal. For example, transducer 202 may be configured to generate a second signal representative of a baseline mechanical wave of MCS device 206 without pump thrombosis (e.g., during a predetermined timeframe after implanting MCS device 206 in patient 112). The at least one feature of the dictionary of features may include the second signal. For example, processing circuitry 263 may determine an indication of pump thrombosis when the signal and the second signal differ by a predetermined amount (e.g., a threshold value). Processing circuitry 263 may derive the threshold based at least in part on the signal, the second signal, or both. For example, the threshold value may be a predetermined percent increase in the amplitude of a selected frequency range of the second signal. In this way, processing circuitry 263 may be configured to determine the indication of pump thrombosis based on the signal and a second signal, a threshold, or both. In some examples, at least one feature of the dictionary of features may be associated with a known MCS device operation with pump thrombosis or predicted MCS device operation with pump thrombosis. For example, computing device 204 may retrieve from pump thrombosis detection platform 260 at least one feature of the dictionary of features associated with a clinically confirmed pump thrombosis.

Various examples have been described. These and other examples are within the scope of the claims.

The invention claimed is:

1. An implantable medical device comprising:
communication circuitry;
a transducer configured to generate a signal representative of a mechanical wave from a mechanical circulatory support device separate from the implantable medical device; and
processing circuitry communicatively coupled to the transducer, wherein the processing circuitry is configured to:
determine an indication of pump thrombosis based on the signal and, based on the indication of pump thrombosis, communicate the indication of pump thrombosis to an external user interface device via the communication circuitry.

2. The implantable medical device of claim 1, wherein the user interface device is configured to display an alert to a user, wherein the alert comprises the indication of pump thrombosis.

3. The implantable medical device of claim 1, wherein the implantable medical device comprises at least one of a pacemaker, an implantable cardioverter-defibrillator, an insertable cardiac monitor, or a cardiac resynchronization therapy device.

4. The implantable medical device of claim 1, wherein the mechanical wave is an acoustic wave or a vibration generated by the mechanical circulatory support device.

5. The implantable medical device of claim 1, wherein the transducer comprises an electromagnetic transducer, an electrostatic transducer, a capacitive micromachined transducer, or a piezoelectric transducer.

6. The implantable medical device of claim 1, wherein, to determine the indication of pump thrombosis, the processing circuitry is configured to:
identify at least one portion of the signal indicative of pump thrombosis;
determine at least one feature of the at least one portion; and
compare the at least one feature to a threshold value.

7. The implantable medical device of claim 6, wherein the at least one feature comprises at least one harmonic of the mechanical wave.

8. The implantable medical device of claim 7, wherein the at least one harmonic comprises the third harmonic of the mechanical wave.

9. The implantable medical device of claim 1, wherein the signal comprises a first signal, wherein the transducer is further configured to generate a second signal representative of a baseline mechanical wave of the mechanical circulatory support device without pump thrombosis.

10. The implantable medical device of claim 9, wherein the processing circuitry is configured to determine the indication of pump thrombosis based on the first signal and the second signal.

11. The implantable medical device of claim 10, wherein the processing circuitry is further configured to:
determine a threshold based on the second signal; and
determine the indication of pump thrombosis based on the first signal and the threshold.

12. A method comprising:
receiving, by processing circuitry of an implantable medical device, a signal from a transducer of the implantable medical device representative of a mechanical wave generated by a mechanical circulatory support device separate from the implantable medical device;
determining, by the processing circuitry, an indication of pump thrombosis based on the signal; and
based on the indication of the pump thrombosis, communicating, by the processing circuitry, the indication of pump thrombosis to an external user interface device.

13. The method of claim 12, further comprising displaying, by the external user interface device an alert to a user, wherein the alert comprises the indication of pump thrombosis.

14. The method of claim 12, wherein the implantable medical device comprises at least one of a pacemaker, an implantable cardioverter-defibrillator, an insertable cardiac monitor, or a cardiac resynchronization therapy device.

15. The method of claim 12, wherein the mechanical wave is an acoustic wave or a vibration generated by the mechanical circulatory support device.

16. The method of claim 12, wherein the transducer comprises an electromagnetic transducer, an electrostatic transducer, a capacitive micromachined transducer, or a piezoelectric transducer.

17. The method of claim 12, wherein determining the indication of pump thrombosis comprises:
identifying at least one portion of the signal indicative of pump thrombosis;
determining at least one feature of the at least one portion; and
comparing the at least one feature to a threshold value.

18. The method of claim 17, wherein the at least one feature comprises at least one harmonic of the mechanical wave.

19. The method of claim 18, wherein the at least one harmonic comprises the third harmonic of the mechanical wave.

20. The method of claim 12, wherein the signal comprises a first signal, the method further comprising receiving, by the processing circuitry, a second signal from the transducer representative of a baseline mechanical wave of the mechanical circulatory support device without pump thrombosis.

21. The method of claim 20, wherein determining the indication of pump thrombosis comprises determining the indication of pump thrombosis based on the first signal and the second signal.

22. The method of claim 21, wherein determining the indication of pump thrombosis based on the first signal and the second signal comprises:
determining a threshold based on the second signal; and
determining the indication of pump thrombosis based on the first signal and the threshold.

* * * * *